United States Patent [19]

Hill

[11] 4,319,185

[45] Mar. 9, 1982

[54] DELAY LINE MICROWAVE MOISTURE MEASURING APPARATUS

[75] Inventor: John H. Hill, Hamilton, Canada

[73] Assignee: Sentrol Systems Ltd., Downsview, Canada

[21] Appl. No.: 100,424

[22] Filed: Dec. 5, 1979

[51] Int. Cl.³ .......................................... G01R 27/04
[52] U.S. Cl. ............................................. 324/58.5 A
[58] Field of Search ............ 324/58.5 A, 58 A, 58 R, 324/58.5 B

[56] References Cited

U.S. PATENT DOCUMENTS

| | | | |
|---|---|---|---|
| 3,155,898 | 11/1964 | Chope | 324/58.5 A |
| 3,534,260 | 10/1970 | Walker | 324/58.5 A |
| 3,815,019 | 6/1974 | Wiles | 324/58.5 A |
| 3,818,333 | 6/1974 | Walker | 324/58.5 A |
| 3,851,244 | 11/1974 | Mounce | 324/58.5 A |
| 4,123,702 | 10/1978 | Kinanen et al. | 324/58.5 A |
| 4,211,970 | 7/1980 | Fitzky | 324/58.5 A X |

FOREIGN PATENT DOCUMENTS

| | | | |
|---|---|---|---|
| 2373792 | 7/1978 | France | 324/58.5 A |
| 444052 | 5/1975 | U.S.S.R. | 324/58.5 A |

Primary Examiner—Stanley T. Krawczewicz
Attorney, Agent, or Firm—Shenier & O'Connor

[57] ABSTRACT

Microwave moisture measuring apparatus in which a plurality of transmitting antennas direct microwave radiation through individual portions of a moisture-containing sheet material to respective receiving antennas coupled to a common detector. A microwave pulse is provided to one end of a transmission line containing delay elements to provide successively delayed pulses to the transmitting antennas. The delayed pulses are separately received by the detector and analyzed to permit individual measurement of the moisture content of the sheet material portions.

18 Claims, 3 Drawing Figures

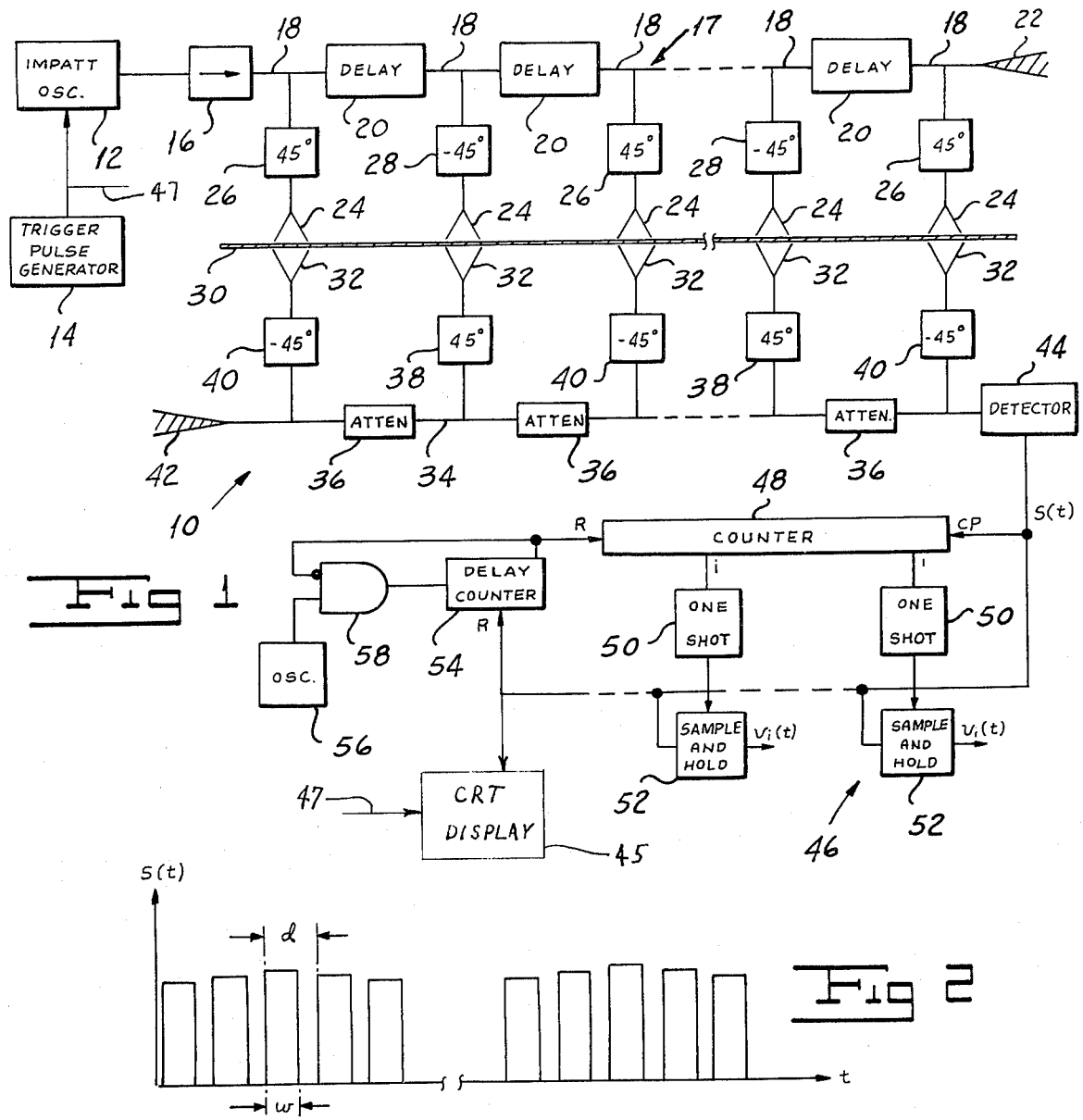
Fig 1
Fig 2
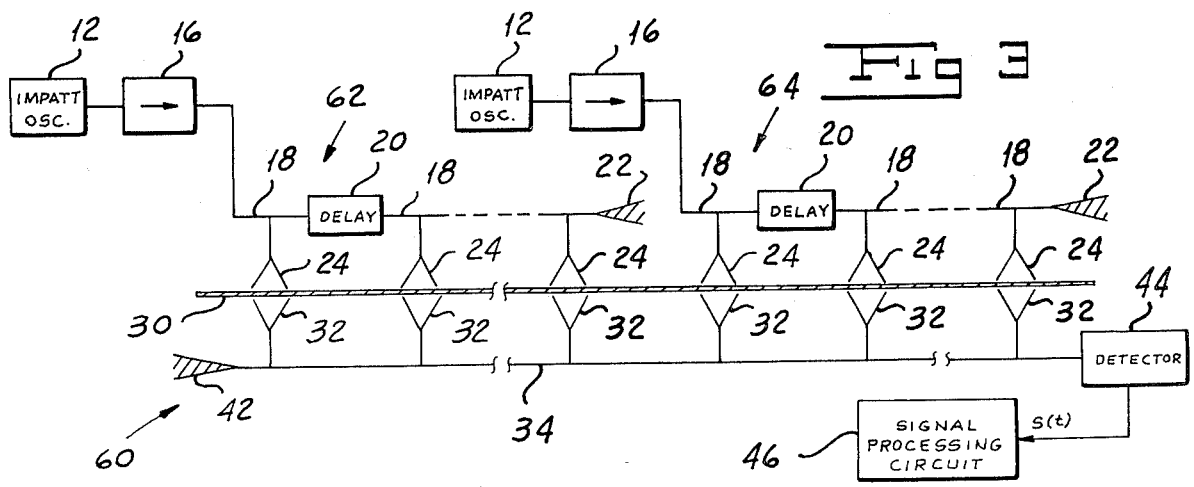
Fig 3

DELAY LINE MICROWAVE MOISTURE MEASURING APPARATUS

BACKGROUND OF THE INVENTION

Accurate process control of a paper-making machine requires on-line measurement of certain paper web properties, the most significant of which are basis weight and moisture. These measurements are traditionally achieved by mounting sensors on a platform which scans the paper web transversely of its length. The web can be moving at any speed from a few hundred to several thousand feet per minute.

Microwave moisture sensors of the prior art operate on the principle that water molecules exhibit a resonant absorption, owing to rotational transition at 22 gigahertz (GHz). By monitoring the absorption of energy at this frequency by the water in the web, one obtains a direct measurement of the amount of water present in the web. The principal advantages of this technique are that there is very little interaction between the energy directed to the web and the constituents of the web other than water, and that the sensitivity of the device can be adjusted to span the entire range of water weights found on paper and board-producing machines. Typical sensors of this type are described in U.S. Pat. No. 3,815,019 issued to S. T. Wiles and U.S. Pat. No. 3,851,244 issued to G. R. Mounce.

Measurements obtained in the manner described above are usually presented either as an average of the measurement for one complete traversal across the web or as a graph of the measured value of the variable in question as a function of scanner position across the web. This latter form is known as the measured variable's "profile" and is typically displayed on a video screen or as a visible trace on paper. In some instances, the measured profile is used to make automatic adjustments of process condition across the paper machine, but more often manual control is exercised.

This technique of mechanical scanning has two serious drawbacks. Since the web is moving very rapidly and the scanner relatively slowly, the profile obtained in a typical one-minute scan does not represent a true cross-machine picture, but rather a combination of the true profile and variations along the direction of travel of the web. That is, the scanner actually sees a long diagonal on the web. If the machine is running at 2000 feet per minute, in a one-minute scan, 2000 feet of paper will pass the scanner. To obtain a true profile, the scan must be made extremely rapidly. The scanner, which must operate continuously in a very hostile environment, is a complex and expensive device and tends to be a very high-maintenance item. It is not unusual to find that 40 to 50 percent of the system problems are associated with the scanner. Finally, in many installations there is not sufficient space to mount a scanner and therefore a control system cannot be added to the machine.

In an alternative system, disclosed in U.S. Pat. No. 3,534,260 issued to C. W. E. Walker, a plurality of pairs of microwave transmitters and receivers are successively actuated by ferrite or diode switches to scan a plurality of areas of the web electronically in multiplex fashion. While this technique permits profile measurements of moisture along or across the web without mechanical scanners, the switching components entail additional expense and introduce the problems of poor reliability associated with active devices.

SUMMARY OF THE INVENTION

One of the objects of my invention is to provide a moisture sensor which provides profile measurements along or across a paper web.

Another object of my invention is to provide a moisture sensor which provides a profile measurement representing a true sheet cross section.

Still another object of my invention is to provide microwave moisture measuring apparatus which individually measures the moisture content of a plurality of areas of a sheet material without using active elements to effect microwave switching.

A further object of my invention is to provide microwave moisture measuring apparatus which is relatively simple and inexpensive.

Still another object of my invention is to provide a microwave moisture measuring apparatus which is reliable.

Other and further objects of my invention will be apparent from the following description.

In general, my invention contemplates moisture-measuring apparatus in which a plurality of transmission paths through respective regions of the material being analyzed couple a microwave pulse source to a suitable microwave detector. Delay elements contained in the transmission paths provide the paths with effective lengths differing by amounts sufficient to permit recovery of the individual pulses traveling along the paths. Where a plurality of transmitting and receiving antennas are used to direct microwave radiation through the respective regions, the delay elements are preferably provided by coupling successive transmitting or receiving antennas to successive junctions of a train of serially connected delay lines coupled at one end to either the pulse providing means or the detector. By using a microwave pulse together with passive delay elements to cause the individual path pulses to arrive at the detector at different instants of time, I am able to measure the individual moisture contents of a plurality of areas in multiplex fashion without active switching devices. My apparatus is thus simpler and less expensive and does not have the reliability problems associated with active switching components.

BRIEF DESCRIPTION OF THE DRAWINGS

In the accompanying drawings to which reference is made in the instant specification and in which like reference characters are used to indicate like parts in various views:

FIG. 1 is a partly schematic view of one embodiment of my microwave measuring system.

FIG. 2 is a plot of the output of the microwave detector of my apparatus as a function of time.

FIG. 3 is a partly schematic view of an alternative embodiment for use with relatively wide paper webs.

DETAILED DESCRIPTION OF THE PREFERRED EMBODIMENTS

Referring now to FIGS. 1 and 2, my system, indicated generally by the reference character 10, includes a suitable microwave pulse generator 12, such as an IMPATT oscillator, which is periodically triggered by a trigger pulse generator 14 to provide a 22 GHz output pulse. I connect the oscillator 12 to a transmission line indicated generally by the numeral 17 comprising a plurality of parallel waveguide T-junctions 18 serially coupled by delay lines or elements 20. Delay elements 20 effectively form a tapped delay line, successive outputs of which provide delayed pulses in the individual transmission paths to be described. Preferably, turnaround delay lines are used for the delay elements 20 to conserve space. An isolator 16 forms a unidirectional coupling from the oscillator 12 to the line 17.

Rerspective alternate plus 45° and minus 45° waveguide twists 26 and 28 connect the respective verticals of the successive T-junctions along line 17 to transmitting horns 24 arranged to direct radiation on spaced portions of a web 30. Each of the T-junctions 18 is so constructed that most of the radiation entering the cross of the T-section is transmitted down the line 17 while but a small portion is directed through the vertical. To prevent undesirable reflections, each of the ports of the T-junctions should present a matched impedance to its associated transmission line segment. The waveguide twists 26 and 28 provide cross-polarization between adjacent transmitting horns to minimize undesirable cross talk. I terminate the straight-through portion of the final T-junction 18 of the transmission line 17 with a flat, or matched, load 22 of any suitable type to prevent undesirable reflections.

A plurality of receiving horns 32 arranged on the other side of the web 30 from the transmitting horns 24 receive radiation transmitted through the respective web portions. Receiving horns 32 are coupled to a second transmission line comprising a waveguide 34 through respective −45° and +45° twists 40 and 38 to restore the plane of polarization of the microwaves to that of the T-junctions 18. Twists 38 and 40 are joined to the waveguide 34 through parallel T-junctions (not separately indicated) similar to the T-junctions 18. The cross portions of the T-sections may be integral with one another so as to constitute the waveguide 34 itself. Like the T-junctions 18, these latter T-junctions should also present matched impedance to their associated transmission line elements to prevent undesirable reflections. If desired, small attenuating elements 36 may be inserted in the waveguide 34 between the cross portions of the T-sections making up guide 34 to compensate for the losses introduced by delay elements 20 and the straight-through sections of T-junctions 18. I provide a terminating load 42, similar to the load 22, at the other end of guide 34 to prevent undesirable reflections.

A microwave detector 44, such as a diode, disposed at one end of waveguide 34 generates a signal s(t) representing the instantaneous amplitude of the envelope of the microwave signal applied to the detector. Preferably detector 44 is disposed at the end of the waveguide 34 remote from the oscillator 12 to help equalize path losses.

In FIG. 2, I show a plot of the wave form of the detected signal s(t). The signal s(t) comprises spaced pulse groups, each of which consists of successively delayed path pulses from a single oscillator pulse. Thus, the first pulse of each group corresponds to the substantially undelayed oscillator pulse transmitted between the first, or leftmost, pair of antennas 24 and 32, while the second pulse corresponds to the path pulse passing through a single delay element before being transmitted from the second antenna 24, and so on. The amplitudes of the respective pulses of each group vary proportionately with the transmittances of the corresponding portions of the web 30 at 22 GHz. Since these transmittances depend on the amount of water present, the pulse amplitudes provide a direct measure of moisture content at various locations across the width of the web.

Preferably, the width w of the microwave pulse generated by oscillator 12 is between 7 and 8 nanoseconds, while the spacing between the leading edges of the pulses, corresponding to the delay d introduced by the elements 20, is slightly greater than the pulse width, or about 10 nanoseconds. While it is desirable that the spacing of the detected pulses be greater than their width, this is not essential to the operation of my apparatus. In general, the spacing of the pulses need only be sufficient to permit recovery of at least a portion of the individual pulses. Further, while I have shown the delay elements 20 in the upper line 17 coupled to the oscillator 12, the same delay could also be obtained by placing the delay elements 20 in the lower line 34, interchanging the delay elements 20 and attenuators 36.

Finally, while respective pairs of transmitting and receiving horns are used in the various transmission paths in the embodiments shown, those skilled in the art will readily appreciate that contacting sensors such as surface wave absorption cells could also be used. Such surface wave absorption cells, which are shown and described in Wiles U.S. Pat. No. 3,815,019, may be preferable in certain applications, since they may effectively be moved "off sheet" for calibration simply by moving them slightly away from the web.

To maximize the power transmitted by the remote, or rightmost, horn 24 when identical T-junctions 18 are used in lines 17 and 34, each junction should transmit 1/n of the entering line radiation through the side arm and 1−1/n of the entering line radiation along the line 17 or 34, where n is the number of pairs of horns 24 and 32.

The detected signal s(t) is fed to a signal processing circuit, indicated generally by the reference numeral 46, to recover the individual received pulses. The detected signal drives the clock input of a ring counter 48 having one more stage than the number of transmitting or receiving horns. Counter 48 thus has stages 1 through n corresponding to the individual transmitting and receiving horns plus a zero stage to which counter 48 is set between groups of detected signal pulses. Ring counter 48 provides an output on a first line in response to the first pulse of a given group and shifts the output to succeeding lines in response to succeeding pulses.

The outputs of counter 48 drive respective one-shot multivibrator circuits 50, the outputs of which gate respective sample-and-hold circuits 52. The detected signal s(t) is coupled to each of the sample-and-hold circuits 52. One-shot circuits 50 provide pulses having a shorter duration than the detected signal pulses to permit each of the sample-and-hold circuits 52 to sample only that portion of the detected signal s(t) corresponding to a path pulse. Thus, one-shot circuit 50 coupled to the first output of counter 48 samples the first pulse to provide an output signal $v_1(t)$. More generally, the one-shot circuit 52 connected to the ith output of counter 48 samples the ith path pulse to provide an output signal $v_i(t)$. In this manner, circuit 46 provides individual outputs $v_1(t)$ through $v_n(t)$ corresponding to the respective pulses transmitted through the individual sheet portions. If desired, the detector output s(t) may also be coupled directly to a suitable display such as a cathode ray tube (CRT) 45, the trigger input of which is supplied by a line 47 coupled to the trigger pulse generator 14.

Suitable calibrating means such as potentiometers (not shown) may be used to adjust the individual outputs from circuits 52 to compensate for any residual differences in path loss not compensated for by attenuators 36. Such potentiometers may also be used to compensate for losses introduced by delay elements 20 and the straight-through sections of T-junctions 18 if attenuators are not used.

A reset circuit associated with the ring counter 48 includes a counter 54 receiving a reset input from detector 44 and receiving a clock input from a 100 MHz oscillator 56 through an AND gate 58. Counter 54 is thus reset at a 100 MHz rate by pulses from detector 44 but is clocked at the same rate by oscillator 56. Thus during detection of a pulse group, the output of counter 54 varies between zero and one. After the last pulse of a group has been detected, counter 54 is indexed by oscillator 56 to a two output. This two output is applied to the reset terminal of ring counter 48, resetting that counter, and also applied to an inhibiting input of AND gate 58 to prevent further clocking of the counter 54. Oscillator 56 is again permitted to clock counter 54 after the counter 54 is reset by the first pulse of a succeeding group.

In most applications, only a single tapped delay line 17 is required. However, if an extremely large number of measurements is required, the attenuation is large and the signal-to-noise ratio of the detector is correspondingly reduced, resulting in unreliable or inaccurate measurements. In such instances, it may be preferable to use the alternative system 60 shown in FIG. 3, in which I divide the upper transmission line into two sections 62 and 64 and apply signals to the ends of the sections 62 and 64 from separate pulse oscillators 12 through respective isolators 16. The oscillators 12 are pulsed by any suitable means (not shown) in alternating fashion to produce a detected signal s(t) from detector 44 comprising alternating groups of pulses transmitted through the respective sections 62 and 64.

The detected signal s(t) is fed to a signal processing circuit which may be identical to the circuit 46 of FIG. 1. The ring counter 48 in such a circuit would have one more stage than the total number of transmitting or receiving horns. In order to use the reset circuit shown in FIG. 1, the pulsing of the oscillators 12 should be so timed that the second group of pulses follows the first group by a time interval insufficient to cause the counter 48 to be reset. A longer period of time sufficient to allow the counter 48 to be reset should intervene between the end of the second group of pulses and the beginning of the first group.

It will be seen that I have accomplished the objects of my invention. My apparatus individually measures the moisture content of a plurality of areas of a sheet material without using active microwave switching elements. My apparatus is relatively simple and inexpensive. My apparatus does not have the problems of reliability associated with active microwave switching devices.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention, what I claim is:

1. Apparatus for measuring the moisture content of each of a plurality of regions of a material including in combination means for providing a pulse of microwave energy having a certain plane of polarization, a detector, means for providing a first transmission path from the pulse means to the detector, means for producing a first time delay, and means including the delay means for providing a second transmission path from the pulse means to the detector, said transmission paths having respective parallel portions affected by the moisture contents of respective first and second regions of said material, one transmission path including means for radiating microwave energy with a plane of polarization shifted by $+45°$ and the other transmission path including means for radiating microwave energy with a plane of polarization shifted by $-45°$.

2. Apparatus for measuring the moisture content of each of a plurality of regions of a material including in combination means for providing a pulse of microwave energy, a detector, means for providing a first transmission path from the pulse means to the detector, said first transmission path including means for radiating microwave energy with a certain polarization, means for producing a first time delay, and means including the delay means for providing a second transmission path from the pulse means to the detector, said transmission paths having respective parallel portions affected by the moisture contents of respective first and second regions of said material, said second transmission path including means for radiating microwave energy with an orthogonal polarization.

3. Apparatus for measuring the moisture content of each of a plurality of regions of a material including in combination means for providing a pulse of microwave energy, said pulse having a certain duration, a detector, means for providing a first transmission path from the pulse means to the detector, means for producing a first time delay greater than said pulse duration, and means including the delay means for providing a second transmission path from the pulse means to the detector, said transmission paths having respective parallel portions affected by the moisture contents of respective first and second regions of said material.

4. Apparatus for measuring the moisture content of each of a plurality of regions of a material including in combination means for providing a pulse of microwave energy, a detector, means for providing a first transmission path from the pulse means to the detector, means for producing a first time delay, and means including the delay means for providing a second transmission path from the pulse means to the detector, said transmission paths having respective parallel portions affected by the moisture contents of respective first and second regions of said material.

5. Apparatus as in claim 4 further including means for producing a second time delay and means including the first and second delay means for providing a third transmission path from the pulse means to the detector, said third transmission path having a portion parallel to said first and second path portions and affected by the moisture content of a third region of said material.

6. Apparatus as in claim 4 wherein each transmission path includes a transmitting horn antenna and a corresponding receiving horn antenna.

7. Apparatus for measuring the moisture contents of a plurality of regions of a material including in combination means for providing a pulse of electromagnetic energy, a detector, means for providing a first transmission path between said pulse means and said detector, a first time delay element, and means including said delay element for providing a second transmission path between said pulse means and said detector, said transmission paths having respective parallel portions affected by the moisture contents of respective first and second regions of said material.

8. Apparatus as in claim 7 further including a second time delay element and means including the first and second delay elements for providing a third transmission path between said pulse means and said detector, said third transmission path having a portion parallel to said first and second path portions and affected by the moisture content of a third region of said material.

9. Apparatus as in claim 7 wherein the pulse means provides microwave energy of approximately 22 gigahertz.

10. Apparatus for analyzing a plurality of regions of material including in combination means for providing a pulse of electromagnetic energy, a detector, means for providing respective transmission paths having respective parallel portions through said regions between said pulse means and said detector, and means comprising a plurality of serially connected time delay elements for providing the transmission paths with appreciably different effective lengths.

11. Apparatus for analyzing a plurality of regions of a material including in combination means for providing a pulse of electromagnetic energy, a detector, means for providing respective transmission paths having respective parallel portions through said regions between said pulse means and said detector, said path providing means comprising a plurality of pairs of transmitting and receiving antennas arranged in an array, adjacent antennas of said array being cross-polarized relative to each other, and means providing the transmission paths with appreciably different effective lengths.

12. Apparatus for analyzing a plurality of regions of a material including in combination means for providing a pulse of electromagnetic energy, a detector, means for providing respective transmission paths having respective parallel portions through said regions between said pulse means and said detector, and means providing the transmission paths with appreciably different effective lengths.

13. Apparatus as in claim 12 for measuring the moisture content of the material wherein the pulse means provides microwave energy of approximately 22 gigahertz.

14. Apparatus as in claim 12 wherein said path providing means comprises a plurality of pairs of transmitting and receiving antennas.

15. Apparatus as in claim 14 wherein the path providing means comprises a plurality of horn antennas.

16. Apparatus as in claim 14 wherein the path providing means comprises a plurality of pairs of horn antennas.

17. Apparatus for measuring the moisture content of each of a plurality of regions of a sheet material including in combination a source of microwave energy, a detector, and completely passive stationary coupling means for providing respective transmission paths having respective parallel portions affected by the moisture content of said regions between said source and said detector, said source and said coupling means being so constructed that microwave energy traveling along each of said transmission paths arrives at said detector at a different instant of time.

18. Apparatus for analyzing a plurality of regions of a material including in combination means for providing a pulse of electromagnetic energy, a detector, means for providing a first transmission path between said pulse means for said detector, a time delay element, and means including said delay element for providing a second transmission path between said pulse means and said detector, said transmission paths having respective parallel portions affected by respective first and second regions of said material.

* * * * *

UNITED STATES PATENT AND TRADEMARK OFFICE
CERTIFICATE OF CORRECTION

PATENT NO. : 4,319,185
DATED : March 9, 1982
INVENTOR(S) : John H. Hill

It is certified that error appears in the above-identified patent and that said Letters Patent are hereby corrected as shown below:

Column 8, line 34, "for" should read -- and --.

Signed and Sealed this

Fourth Day of May 1982

[SEAL]

Attest:

GERALD J. MOSSINGHOFF

Attesting Officer     Commissioner of Patents and Trademarks